(12) United States Patent
Jobic

(10) Patent No.: US 7,604,813 B2
(45) Date of Patent: Oct. 20, 2009

(54) WOOD ADHESIVE COMPRISING AN INSECTICIDE

(75) Inventor: Sylvestre Jobic, Alix (FR)

(73) Assignee: BASF Agro B.V., Arnhem (NL), Wadenswil (CH)

( * ) Notice: Subject to any disclaimer, the term of this patent is extended or adjusted under 35 U.S.C. 154(b) by 366 days.

(21) Appl. No.: 11/086,514

(22) Filed: Mar. 22, 2005

(65) Prior Publication Data

US 2005/0233138 A1   Oct. 20, 2005

Related U.S. Application Data

(63) Continuation of application No. 09/155,843, filed as application No. PCT/FR97/00605 on Apr. 3, 1997, now abandoned.

(30) Foreign Application Priority Data

Apr. 9, 1996 (FR) .................................. 96 04694
Apr. 9, 1996 (FR) .................................. 96 04695

(51) Int. Cl.
*A01N 25/00* (2006.01)
*A01N 43/56* (2006.01)
*B32B 21/04* (2006.01)

(52) U.S. Cl. ..................... 424/405; 514/406; 428/537.1

(58) Field of Classification Search ................. 424/405; 514/406; 428/537.1
See application file for complete search history.

(56) References Cited

FOREIGN PATENT DOCUMENTS

| | | |
|---|---|---|
| DE | 3536417 | 4/1987 |
| DE | 4414333 | 10/1995 |
| EP | 0295117 | 12/1988 |
| EP | 0500209 | 8/1992 |
| JP | 52127936 | 10/1977 |
| JP | 0517732 | 1/1993 |
| JP | 05152003 A | * 6/1993 |
| WO | 9306089 | 4/1993 |
| WO | 9522902 | 8/1995 |

OTHER PUBLICATIONS

JP 52-127936 English translation.*
JP 55-152003 English translation.*
JP 05-017732 English translation.*
Chemical Abstracts, vol. 92, No. 11, abstract No. 89272, Mar. 17, 1980.
Chemical Abstracts, vol. 99, No. 14, abstract No. 106972, Oct. 3, 1983.
Chemical Abstracts, vol. 107, No. 9, abstract No. 72897, Aug. 31, 1987.
Chemical Abstracts, vol. 115, No. 21, abstract No. 226176, Nov. 25, 1991.
Chemical Abstracts, vol. 124, No. 21, abstract No. 282013, May 20, 1996.
Database WPI, Derwent Publications abstract No. 77-872784.
Database WPI, Derwent Publications abstract No. 81-06781D.
Database WPI, Derwent Publications abstract No. 85-034300.
Database WPI, Derwent Publications, abstract No. 93-203343.
Database WPI, Derwent Publications abstract No. 96-149245.
Patent Abstracts of Japan, vol. 95, No. 9, Oct. 31, 1995.
BASF Material Safety Data Sheets of Mar. 1987 (original in German and certified English translation).
Bobe et al. "Factors Influencing the Adsorption of Fipronil on Soils" 1997, *J. Agric. Food Chem.*, 45:4861-5.
Bobe et al. "Kinetics and Mechanisms of Abiotic Degradation of Fipronil (Hydrolysis and Photolysis)" 1998, *J. Agric. Food Chem.*, 46:2834-9.
Fipronil, New Pesticide Fact Sheet, US EPA Office of Prevention, Pesticides and Toxic Substances, www.fluridealert.org/pesticides/fipronil.epa.facts.may.1996.htm, 1996, 1-6.
Pizzi "Advanced Wood Adhesives Technology" 1994, pp. 92, 112.
Ramesh et al. "Kinetics and Hydrolysis of Fenamiphos, Fipronil, and Trifluralin in Aqueous Buffer Solutions" 1999, *J. Agric. Food Chem.*, 47:3367-71.

* cited by examiner

*Primary Examiner*—Shengjun Wang
(74) *Attorney, Agent, or Firm*—Baker Botts L.L.P.

(57) ABSTRACT

A wood glue containing 1-(hetero)arylpyrazole-type active insecticide material and wooden materials bonded with a glue containing said active insecticide material are disclosed.

7 Claims, No Drawings

WOOD ADHESIVE COMPRISING AN INSECTICIDE

The present application is a continuation of U.S. patent application Ser. No. 09/155,843, filed Oct. 16, 1998 now abandoned, which is a national stage application of International Patent Application No. PCT/FR97/00605, filed on Apr. 3, 1997, each of which is incorporated by reference into the instant specification in its entirety.

The present invention relates to the field of adhesives intended to bond wood and comprising an insecticide.

Adhesives intended for the bonding of wood or of wood particles are widely known.

These wood adhesives are generally of polymeric type, in particular based on thermoplastic or thermosetting polymers.

These wood adhesives are applied in many fields and in particular in the production of wood-based materials and more specifically wood-based materials of chipboard, plywood, laminate or veneer type and the like.

These materials are used in the construction of buildings, houses and blocks of flats, as well as in fitting out the said buildings, houses and blocks of flats, such as, for example, furniture.

Moreover, it is known that these materials are the subject of attacks by insects, in particular termites.

In point of fact, the number of products which can be used in practice for protecting wood against attacks by insects, in particular termites, is rather limited, all the more so since several of them have been dropped for reasons of environmental protection, such as, for example, the so-called organochlorinated products.

The need thus remains for wood adhesives conferring protection against insects, in particular termites, on materials based on bonded wood.

One aim of the invention is to meet the existing requirements as regards adhesives comprising an insecticide which are involved in the manufacture of wood-based materials.

Another aim of the invention is to provide adhesives for the manufacture of wood-based materials which do not have the disadvantages of the known products.

Another aim of the invention is to provide adhesives for the manufacture of wood-based materials which are resistant to insects, in particular to termites.

Another aim of the invention is to provide wood-based materials which are resistant to insects, in particular to termites.

Another aim of the invention is to provide wood-based materials of chipboard, plywood, laminate or veneer type which are immunized against perforations caused by insects.

It has now been found that these aims could be achieved, in all or in part, by virtue of the wood adhesives according to the invention.

The invention consequently relates to wood adhesives comprising an insecticidal active material of formula (I):

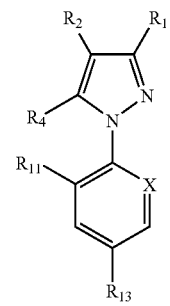

in which:
$R_1$ is CN or methyl;
$R_2$ is $S(O)_n R_3$;
$R_3$ is alkyl or haloalkyl;
$R_4$ represents a hydrogen or halogen atom or an $NR_5 R_6$, $-S(O)_n R_7$, $-C(O)R_7$ or $-C(O)O-R_7$, alkyl, haloalkyl or $-OR_8$ radical or an $-N=C(R_9)(R_{10})$ radical;
$R_5$ and $R_6$ represent, independently of one another, the hydrogen atom or an alkyl, haloalkyl, $-C(O)$alkyl or $-S(O)_r CF_3$ radical or alternatively $R_5$ and $R_6$ can together form a divalent alkylene radical which can be interrupted by one or two divalent heteroatoms, such as oxygen or sulphur;
$R_7$ represents an alkyl or haloalkyl radical;
$R_8$ represents an alkyl or haloalkyl radical or the hydrogen atom;
$R_9$ represents an alkyl radical or the hydrogen atom;
$R_{10}$ represents a phenyl or heteroaryl group optionally substituted by one or a number of halogen atoms or groups such as $-OH$, $-O$-alkyl, $-S$-alkyl, cyano or alkyl;
$R_{11}$ and $R_{12}$ represent, independently of one another, a hydrogen or halogen atom;
$R_{13}$ represents a halogen atom or a haloalkyl, haloalkoxy, $-S(O)_q CF_3$ or $-SF_5$ group;
m, n, q and r represent, independently of one another, an integer equal to 0, 1 or 2;
X represents a trivalent nitrogen atom or a $C-R_{12}$ radical, the other three valencies of the carbon atom forming part of the aromatic ring;
with the proviso that, when $R_1$ is methyl, then $R_3$ is haloalkyl, $R_4$ is $NH_2$, $R_{11}$ is Cl, $R_{13}$ is $CF_3$ and X is N.

The term "alkyl" present in the definitions of the radicals of the compound of formula (I) represents a linear or branched alkyl radical containing from 1 to 6 carbon atoms.

The term "alkoxy" present in the definitions of the radicals of the compound of formula (I) represents a linear or branched alkoxy radical containing from 1 to 6 carbon atoms.

The term "alkylene" present in the definitions of the radicals of the compound of formula (I) represents an alkylene radical containing from 1 to 4 carbon atoms.

The term "halogen" and the prefix "halo-" present in the definitions of the radicals of the compound of formula (I) mean respectively fluorine, chlorine, bromine or iodine and fluoro-, chloro-, bromo- or iodo-.

The term "heteroaryl" present in the definitions of the radicals of the compound of formula (I) represents an aromatic radical containing 5 or 6 atoms, one or a number among which can optionally be chosen from nitrogen, oxygen and sulphur.

A preferred class of compounds of formula (I) is composed of the compounds such that $R_1$ is CN and/or $R_3$ is haloalkyl and/or $R_4$ is $NH_2$ and/or $R_{11}$ and $R_{12}$ are, independently of one another, a halogen atom and/or $R_{13}$ is haloalkyl.

A compound of formula (I) which is very particularly preferred in the present invention is 1-[2,6-$Cl_2$-4-$CF_3$-phenyl]-3-CN-4-[SO—$CF_3$]-5-$NH_2$-pyrazole, hereinafter known as Compound A.

Compounds of formula (I) can be prepared according to one or other of the processes described in Patent Applications WO-A-87/3781, WO-A-93/6089, WO-A-94/21606 or EP-A-295,117 or any other process coming within the competence of the person skilled in the art who is a specialist in chemical synthesis.

The invention consequently relates to wood adhesives containing an insecticide of formula (I).

In the present invention, wood adhesives is understood to mean adhesives, binding or bonding agents or glues intended for the bonding of wood, whether in the form of sheets, laths, particles, and the like, to itself or to another substrate.

The wood adhesives which are used as base in the preparation of the wood adhesives containing an insecticide according to the invention are those known to the person skilled in the art and more particularly adhesives based on thermosetting resins and adhesives based on thermoplastic resins.

Adhesives based on thermosetting resins confer high mechanical strength on the materials and for this reason are more particularly used in the production of materials for furniture or frameworks.

Mention may be made, among adhesives based on thermosetting resins used in the present invention, without implied limitation, of urea-formaldehyde adhesives, phenol-formaldehyde adhesives, resorcinol-formaldehyde adhesives, melamine-formaldehyde adhesives and silicone adhesives.

By way of example, the phenol-formaldehyde adhesives will be used more particularly in the production of plywoods. Resorcinol-formaldehyde adhesives will be preferred, because of their excellent resistance to ageing and to weathering, for example for the manufacture of materials which can be used externally and/or which require a high guarantee of stability with respect to the weather.

Mention may be made, among adhesives based on thermoplastic resins, without implied limitation, of vinyl adhesives and polyacrylic adhesives.

A type of wood adhesive based on thermoplastic resin which is preferred for the present invention is composed of vinyl adhesives, for example vinyl resins, in particular poly(vinyl acetate), or, for example, adhesives based on acetochlorides, poly(vinyl alcohol), poly(vinyl acetal)s, poly(vinyl ether)s or vinyl acetate and more particularly adhesives based on ethylene-vinyl acetate copolymer.

Another category of adhesives to which the present invention relates is composed of elastomer-based adhesives.

The wood adhesives according to the invention can be composed of a single type of adhesive or of a mixture of adhesives (mixed adhesives).

The wood adhesives according to the present invention can be provided in the form of more or less viscous or pasty liquids, in the form of aqueous or alcoholic solutions, as emulsions, in the form of powders which are soluble in water or alcohol or in the form of films which can be applied directly. Finally, in the case of adhesives based on thermoplastic resins, these can be provided in the form of heat-fusible preparations.

The combined adhesives described above constitute a non-limiting list. It is clearly understood that any type of adhesive which is suitable for the bonding of wood is suitable for the present invention. As a general rule, the choice of the wood adhesive will be determined by the person skilled in the art who is a specialist in the production of wood-based materials, according to the desired final application of the material.

The wood adhesives according to the invention are prepared by mixing a wood adhesive known per se with an effective amount of insecticidal active material of formula (I).

Effective amount of active material is understood to mean the amount of active material to be mixed with the adhesive so as to obtain wood-based materials which are effectively protected from attacks by insects.

These effective amounts of active material of formula (I) are amounts generally of between 0.5 and 150 g/l, preferably of between 5 and 50 g/l, of wood adhesive. When the wood adhesive according to the invention is packaged in the form of a powder, this is such that the wood adhesive, once in solution or emulsion, contains 0.5 to 150 g/l, preferably 5 to 50 g/l, of insecticidal active material of formula (I).

The invention also relates to wood-based materials composed of a plurality of flat layers of wood and/or of a plurality of wood particles bonded to one another by a wood adhesive comprising an insecticidal active material of formula (I).

In the materials of the invention, the insecticidal active material is thus situated essentially in the adhesive, it being possible for this active material subsequently possibly to migrate in the wood-based material.

The materials based on wood bonded according to the invention are in particular materials based on chipboard, plywood, laminate and veneer.

The wood chipboard materials according to the invention have a thickness generally of between 5 and 100 mm, preferably between 7 and 80 mm.

By way of example, and depending on the final destination of the chipboard-based materials, the thickness will preferably be between 7.5 and 15 mm for the thinnest materials, between 10 and 40 mm for standard materials and between 35 and 80 mm for materials subjected to high stresses.

The particles capable of constituting the wood chipboard materials according to the invention are of a type known per se. They can in particular be fibres, flakes, slices, strips of the most varied lengths, specks, chips, parings, shavings, and the like.

These particles have a size generally varying from a few hundredths of a millimeter to 5 cm. More particularly, their size is advantageously between 0.1 mm and 3 cm, preferably between 0.1 cm and 2.5 cm.

The plywood materials according to the invention are composed of a plurality of flat layers, preferably of 3 to 7 layers. The flat layers capable of constituting the plywood materials according to the invention are positioned with respect to one another so that their fibres are in general directions which cross each other and are even preferentially transverse with respect to one another, generally forming an angle of 90° between them.

Each of the layers has a thickness ranging from 0.5 mm to 2 cm, preferably from 1 mm to 1 cm.

These plywood-based materials can be composites, that is to say contain one or a number of layers of wood chipboard, of paper, of plastic film and the like coming in between the flat layers, or alternatively contain, on one of the faces or both faces, a solid wood or wood chipboard layer, which may or may not be decorative, or alternatively paper.

The final thickness of the plywood-based materials according to the invention is between 1 mm and 10 cm, preferably between 5 mm and 8 cm.

The different thicknesses, particle sizes, number of layers and the like presented above are given by way of information and should not be understood as limits from the viewpoint of the person skilled in the art.

The wood materials according to the invention are obtained in a way which is also known per se, in particular by hot or cold pressing of particles or flat layers with the adhesive, in the presence or absence of a catalyst, according to techniques well known to the person skilled in the art. The type of adhesive and its presentation are also chosen by the person skilled in the art according to the desired final destination of the bonded wood-based material.

According to the invention, the insecticidal active material is situated in this adhesive, which makes possible ready and simple manufacture of the products according to the invention, avoiding in particular the need to treat large volumes of material once in the finished or completed state.

The materials according to the invention are protected against attacks by insects, in particular against attacks of perforating type. As insects capable of generating such attacks, termites are one of the main agents.

The materials according to the invention are thus immunized against perforations originating from insects, in particular termites.

In addition to their immunity against perforations, the materials of plywood, laminate or veneer type according to the invention produce a barrier effect with respect to the passage of insects, in particular termites.

The amount of compound of formula (I) in the wood adhesives according to the invention is an amount which is effective in protecting the bonded wood-based materials against perforations.

These amounts which are effective for protection are amounts which confer on the materials concentrations of active material generally of between 0.05 and 15 $g/m^2$, preferably of between 0.5 and 5 $g/m^2$.

The following examples, given without implied limitation, illustrate the invention and show how it can be put into practice.

EXAMPLE 1

Preparation of an Insecticidal Vinyl Wood Adhesive

An adhesive is prepared by mixing 10 g of the compound (A) with 1 litre of a wood adhesive based on ethylene-vinyl acetate copolymer. This crosslinkable adhesive is used directly in the production of wood chipboard or plywood.

EXAMPLE 2

Preparation of an Insecticidal
Melamine-Formaldehyde Wood Adhesive

An insecticidal adhesive is prepared by mixing a powdered melamine-formaldehyde resin containing 25 g of active material (A) with 1 litre of water. This thermosetting resin can be used in the manufacture of plywood.

EXAMPLE 3

Preparation of a Chipboard

Wood chipboard is prepared by hot compression with the crosslinkable vinyl adhesive described in Example 1. The wood/adhesive ratio is such that the wood chipboard material contains 1 $g/m^2$ of insecticidal active material (A).

A sheet of this wood chipboard with an area of 1 $m^2$ separates two chambers each comprising 200 termites with a choice of feeding and a water supply in order to ensure the survival, whatever happens, of the said termites.

After 21 days, it is observed that the sheet shows no signs either of perforation or of the beginning of perforation.

EXAMPLE 4

Preparation of a Plywood

Plywood is prepared by hot compression with the adhesive described in Example 2. The wood/adhesive ratio is such that the plywood material contains 1 $g/m^2$ of insecticidal active material (A).

A sheet of this plywood with an area of 1 $m^2$ separates two chambers each comprising 200 termites with a choice of feeding and a water supply in order to ensure the survival, whatever happens, of the said termites.

After 21 days, it is observed that the plywood sheet shows no signs either of perforation or of the beginning of perforation.

EXAMPLE 5

Preparation of a Laminate

Laminated wood is prepared by hot compression with the resin described in Example 2. The wood/adhesive ratio is such that the laminated wood material contains 2.5 $g/m^2$ of insecticidal active material (A).

A sheet of the laminated wood with an area of 1 $m^2$ separates two chambers each comprising 200 termites with a choice of feeding and a water supply in order to ensure the survival, whatever happens, of the said termites.

After 21 days, it is observed that the laminated wood sheet shows no signs either of perforation or of the beginning of perforation.

The invention claimed is:

1. An adhesive composition suitable for gluing wood comprising a thermosetting phenol-formaldehyde resin as a wood adhesive and 1-[-2,6-$Cl_2$-4-$CF_3$-phenyl]-3-CN-4-[SO—$CF_3$]-5-$NH_2$-pyrazole (fipronil) in an insecticidal amount.

2. The composition of claim 1 wherein said insects are termites.

3. The composition of claim 1 wherein said fipronil is present in an amount of from 0.5 g/l to 150 g/l.

4. The composition of claim 3 wherein said fipronil is present in an amount of from 5 g/l to 50 g/l.

5. A wood-based material comprising a plurality of wood particles or flat wood layers bonded to one another with the composition of claim 1.

6. The wood-based material of claim 5 wherein said fipronil is present in said wood-based material in an amount of from 0.05 $g/m^2$ to 15 $g/m^2$.

7. The wood-based material of claim 6 wherein said fipronil is present in said wood-based material in an amount of from 0.5 $g/m^2$ to 5 $g/m^2$.

* * * * *

UNITED STATES PATENT AND TRADEMARK OFFICE
CERTIFICATE OF CORRECTION

PATENT NO.        : 7,604,813 B2                                                      Page 1 of 1
APPLICATION NO.   : 11/086514
DATED             : October 20, 2009
INVENTOR(S)       : Sylvestre Jobic It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 713 days.

Signed and Sealed this

Fifth Day of October, 2010

David J. Kappos
*Director of the United States Patent and Trademark Office*